United States Patent [19]

Jellison, Jr. et al.

[11] Patent Number: 5,956,147
[45] Date of Patent: Sep. 21, 1999

[54] TWO MODULATOR GENERALIZED ELLIPSOMETER FOR COMPLETE MUELLER MATRIX MEASUREMENT

[75] Inventors: Gerald E. Jellison, Jr.; Frank A. Modine, both of Oak Ridge, Tenn.

[73] Assignee: Lockheed Martin Energy Research Corporation

[21] Appl. No.: 08/874,365

[22] Filed: Jun. 13, 1997

[51] Int. Cl.[6] .................................................. G01N 21/21
[52] U.S. Cl. ............................................................ 356/369
[58] Field of Search ..................................... 356/364, 365, 356/366, 367, 368, 369; 250/225

[56] References Cited

U.S. PATENT DOCUMENTS

| | | | |
|---|---|---|---|
| 5,247,176 | 9/1993 | Goldstein | 356/367 |
| 5,329,357 | 7/1994 | Bernoux et al. | 356/367 |
| 5,373,359 | 12/1994 | Woollam et al. | 356/369 |
| 5,381,233 | 1/1995 | Chao et al. | 356/369 |
| 5,457,536 | 10/1995 | Kornfield et al. | 356/367 |
| 5,501,637 | 3/1996 | Duncan et al. | 356/367 |

OTHER PUBLICATIONS

S. N. Jasperson, S. E. Schnatterly, "An Improved Method for High Reflectivity Ellipsometry Based On a New Polarization Modulation Technique," *Rev. Sci. Instrum.* 40, 761–767 (1969); 41 152 (1970).

P. S. Hauge, "Recent Developments in Instrumentation in Ellipsometry," *Surf. Sci.* 96 108–140 (1980).

B. Drevillon, J. Perrin, et al "Fast Polarization Modulated Ellipsometer Using a Microprocessor System For Digital Fourier Analysis," *Rev. Sci. Instrum.* 53, 969–977 (1982).

G. E. Jellison, Jr., and F. A. Modine, "Two–Channel Polarization Modulation Ellipsometer," *Appl. Opt.* 29, 959–973.

Richard Anderson, "Measurement of Mueller Matrices," *Appl. Opt.* 31, 11–13 (1992).

*Primary Examiner*—Hoa Q. Pham
*Attorney, Agent, or Firm*—James M. Spicer

[57] ABSTRACT

A two-modulator generalized ellipsometer (2-MGE) comprising two polarizer-photoelastic modulator (PEM) pairs, an optical light source, an optical detection system, and associated data processing and control electronics, where the PEMs are free-running. The input light passes through the first polarizer-PEM pair, reflects off the sample surface or passes through the sample, passes through the second PEM-polarizer pair, and is detected. Each PEM is free running and operates at a different resonant frequency, e.g., 50 and 60 kHz. The resulting time-dependent waveform of the light intensity is a complicated function of time, and depends upon the exact operating frequency and phase of each PEM, the sample, and the azimuthal angles of the polarizer-PEM pairs, but can be resolved into a dc component and eight periodic components. In one embodiment, the waveform is analyzed using a new spectral analysis technique that is similar to Fourier analysis to determine eight sample Mueller matrix elements (normalized to the $m_{00}$ Mueller matrix element). The other seven normalized elements of the general 4×4 Mueller matrix can be determined by changing the azimuthal angles of the PEM-polarizer pairs with respect to the plane of incidence. Since this instrument can measure all elements of the sample Mueller matrix, it is much more powerful than standard ellipsometers.

22 Claims, 3 Drawing Sheets

TWO MODULATOR GENERALIZED ELLIPSOMETER FOR COMPLETE MUELLER MATRIX MEASUREMENT

The United States Government has rights in this invention pursuant to contract no. DE-AC05-96OR22464 between the United States Department of Energy and Lockheed Martin Energy Research Corporation.

FIELD OF THE INVENTION

This invention relates to generalized ellipsometry or Mueller matrix polarimetry, and more particularly to a two-modulator generalized ellipsometer incorporating two polarizer-photoelastic modulator (PEM) pairs, and capable of measuring all sixteen elements of the sample Mueller matrix.

BACKGROUND OF THE INVENTION

Any light beam can be described by a four-element Stokes vector, which describes the polarization of the light beam and its intensity. For an optical measurement that conserves incident photon energy, any interaction of a sample with a polarized light beam described by a Stokes vector will result in another light beam, also described by a four-element Stokes vector. In the general case, sixteen parameters (a 4×4 Mueller matrix) are required to describe this interaction.

In most cases, these sixteen elements are not unique. For example, if the sample is isotropic and the experiment is set up as a reflection ellipsometer, then only three Mueller matrix elements are unique. However, if the sample is not isotropic, or if there are optical elements other than an isotropic sample between the polarization state generator (PSG) and the polarization state detector (PSD), then a larger number of the Mueller matrix elements are non-zero and are unique.

Reflection ellipsometers are optical instruments commonly used to characterize thin films and the optical properties of bulk materials. A defining characteristic of these instruments is that a light beam from the PSG is reflected from the sample surface at a large angle of incidence. The light beam can be either of a single wavelength (usually using a laser as an illumination source), or spectroscopic (usually using a white light source in conjunction with a monochromator). The PSG and the PSD typically contain linear polarizers and possibly optical compensating elements such as quarter-wave plates, Fresnel rhombs, or photoelastic modulators. Most ellipsometers measure one to three independent parameters that are related to linear combinations of Mueller matrix elements. For isotropic samples where there is no significant perturbation of the light beam between the sample and either the PSG or the PSD (such as vacuum chamber windows), two or three independent parameters are often sufficient to characterize the sample. However, if the sample is anisotropic, or if there are additional optical elements between the sample and the PSG and the PSD, then these instruments are not sufficient to characterize the sample. For example, the rotating analyzer ellipsometer (which has a stationary polarizer as the PSG and a rotating polarizer as the PSD), and the rotating polarizer ellipsometer (which has a stationary polarizer as the PSD and a rotating polarizer as the PSG) each measure two independent parameters.

Polarization modulation ellipsometers (which contain a polarizer-photoelastic modulator pair in either the PSG or the PSD, and a polarizer in the other), also measure only two independent parameters, but the third parameter can be measured using a different azimuthal orientation of the polarizer (S. N. Jasperson and S. E. Schnatterly, "An Improved Method for High Reflectivity Ellipsometry Based on a New Polarization Modulation Technique," Rev. Sci. Instrum. 40, 761–767 (1969); 41 152 (1970).); (B. Drevillon, J. Perrin, R. Marbot, A. Violet, and J. L. Dalby, "Fast Polarization Modulated Ellipsometer Using a Microprocessor System for Digital Fourier Analysis," Rev. Sci. Instrum. 53, 969–977 (1982).). The two-channel spectroscopic polarization modulation ellipsometer (which contains a polarizer-photoelastic modulator pair as the PSG and a Wollaston prism as the PSD), (G. E. Jellison, Jr. and F. A. Modine, "Two-Channel Polarization Modulation Ellipsometer," Appl. Opt. 29, 959–973 (1990).) measures three independent parameters simultaneously when the azimuthal angle of the PSG is set to ±22.5° or to ±67.5° with respect to the plane of incidence defined by the sample surface.

Transmission ellipsometers are similar to reflection ellipsometers, except that the incident light passes through the sample. This complicates the analysis since sample thickness variations can partially depolarize the incident beam. The subclass of transmission ellipsometers encompasses several instruments that are designed for certain specific measurement tasks. Dichrographs, for example, are used to measure the difference in optical absorption between the fast and slow axis directions of linearly dichroic materials or to measure the difference in optical absorption for left-and right-circularly polarized light by chiral optical materials.

Other instruments measure linear or circular birefringence. These instruments typically measure only one element of the sample Mueller matrix, which is then interpreted to obtain a specific piece of information. Sacharimeters, for example, measure the rotation of the plane of polarization of a linearly polarized beam by a solution, and they are employed to measure sugar concentration. A sacharimeter can be as simple as a light beam from a laser passing through a polarizer, the sample, another polarizer and then detected, where the azimuthal angle of one of the polarizers is changed to minimize the light reaching the detector. The sugar concentration is determined by measuring the extinction position with the sample in place compared to the extinction position when the sample is removed.

Perturbation spectrometers of various types are also optical instruments that can be generally classified as ellipsometers. In such spectrometers, an optical anisotropy is induced in a sample by applying a perturbation such as an electrical or magnetic field or mechanical stress. The methods and instrumentation of ellipsometry are then used to measure the perturbed optical properties. Instruments that measure Faraday rotation are one such example.

Instruments that can measure the entire Mueller matrix of a sample have been proposed and built previously. One such instrument is the two-compensator ellipsometer (2CE) (P. S. Hauge, "Recent Developments in Instrumentation in Ellipsometry," Surf Sci. 96 108–140 (1980).). It uses rotating fixed-wavelength compensators, so significant data corrections are required to operate the instrument at wavelengths other than the design wavelength. The term "generalized ellipsometer" has been used to describe these and other instruments that measure more parameters than are measured with conventional ellipsometers.

Ellipsometers based on two polarizer-photoelastic modulator pairs have been postulated by Hauge (P. S. Hauge, "Recent Developments in Instrumentation in Ellipsometry,"

Surf. Sci. 96 108–140 (1980).) and by Anderson (Richard Anderson, "Measurement of Mueller Matrices," Appl. Opt. 31, 11–13 (1992).), which in principal would be capable of measuring eight normalized Mueller matrix elements. However, prior to our invention, herein described, no one has described an instrument based on two free running PEMs due to the instrumental complexity and the difficulty of interpreting the waveform. If such an ellipsometer could be built, all 15 normalized Mueller matrix elements could be measured with four measurements at different azimuthal angles of the PSG and the PSD.

Thus, prior to our invention, there has been no practical realization of an ellipsometer based upon two free-running PEMs. The PEMs are resonant devices (with a Q often exceeding 10,000), so their operating frequencies and relative phases are not settable but rather determined from other factors such as the shapes of the PEMs and their operating temperatures. Hereinbelow, we describe an apparatus and method for analyzing the waveform from two free-running photoelastic modulators, thereby providing a realizable and accurate two-modulator generalized ellipsometer.

SUMMARY OF THE INVENTION

It is an object of the present invention to provide a generalized ellipsometer that incorporates two photoelastic modulator-polarizer pairs operating at different resonant frequencies, one acting as the PSG and the other as the PSD.

Another object of the present invention is to provide an ellipsometer that is capable of measuring all sixteen Mueller matrix elements of a sample.

Another object of this invention is to provide an ellipsometer that is capable of measuring all the Mueller matrix elements of a sample normalized to the $m_{oo}$ component of an intervening optical sample when used in either a reflection or a transmission mode A further object of the invention is to provide an ellipsometer that is capable of measuring up to eight Mueller matrix elements simultaneously.

A further object of the invention is to provide a method for analyzing the complicated light beam intensity from an ellipsometer containing two free running photoelastic modulators.

A yet further object of the invention is to provide a method for simultaneously measuring the eight parameters of the sample Mueller matrix that are sufficient to completely characterize many optical samples, when complete measurement of the Mueller matrix is redundant.

In accordance with a first preferred embodiment of the present invention there is provided a two-modulator generalized ellipsometer for measuring up to all sixteen time-independent Mueller matrix elements of a sample comprising: a means for producing a light beam; a polarization state generator (PSG) comprising a polarizer-photoelastic modulator (PEM) pair operating at a first resonant frequency for dynamically elliptically polarizing the light beam before interaction with the sample; a polarization state detector (PSD) comprising a photoelastic modulator(PEM)-polarizer pair operating at a second resonant frequency for polarizing the light beam after interaction with the sample, the resonant frequency of the PSD PEM differing from that of the PSG PEM; a light detector for detecting the time-dependent intensity of the light beam from the PSD and converting the intensity to a time-dependent electrical waveform; and a means for analyzing the time-dependent electrical waveform when the PSG and PSD are unsynchronized.

In accordance with a second preferred embodiment of the present invention there is provided a method for determining up to nine of the sixteen time-independent Mueller matrix elements of a sample comprising the steps of: providing a light beam; dynamically elliptically polarizing the light beam using a polarizer-photoelastic modulator (PEM) pair as a polarization state generator (PSG); impinging the dynamically elliptically polarized light beam onto the sample for interaction therewith to change the polarization of the light beam exiting the sample; dynamically changing the polarization of the light beam exiting the sample using a photoelastic modulator (PEM)-polarizer pair as a polarization state detector (PSD) resulting in a time-dependent light beam exiting from the PSD; monochromatizing the light beam from the PSD to a band of wavelengths using a monochromator; converting the time-dependent light beam intensity from the monochromator to a time-dependent electrical waveform by means of a light detector; and analyzing the time-dependent electrical waveform to determine up to nine time-independent intensity coefficients, which are linear combinations of the sixteen time-independent Mueller matrix elements of the sample.

DESCRIPTION OF THE DRAWINGS

FIG. 2 is a schematic drawing of the polarizer-PEM pair, which make up the polarization state generator, or PSG, (light beam going from left to right). FIG. 2 is also illustrative of the polarization state detector, or PSD, (light beam going from right to left) according to the present invention.

DETAILED DESCRIPTION OF THE PREFERRED EMBODIMENTS

Figure 1:
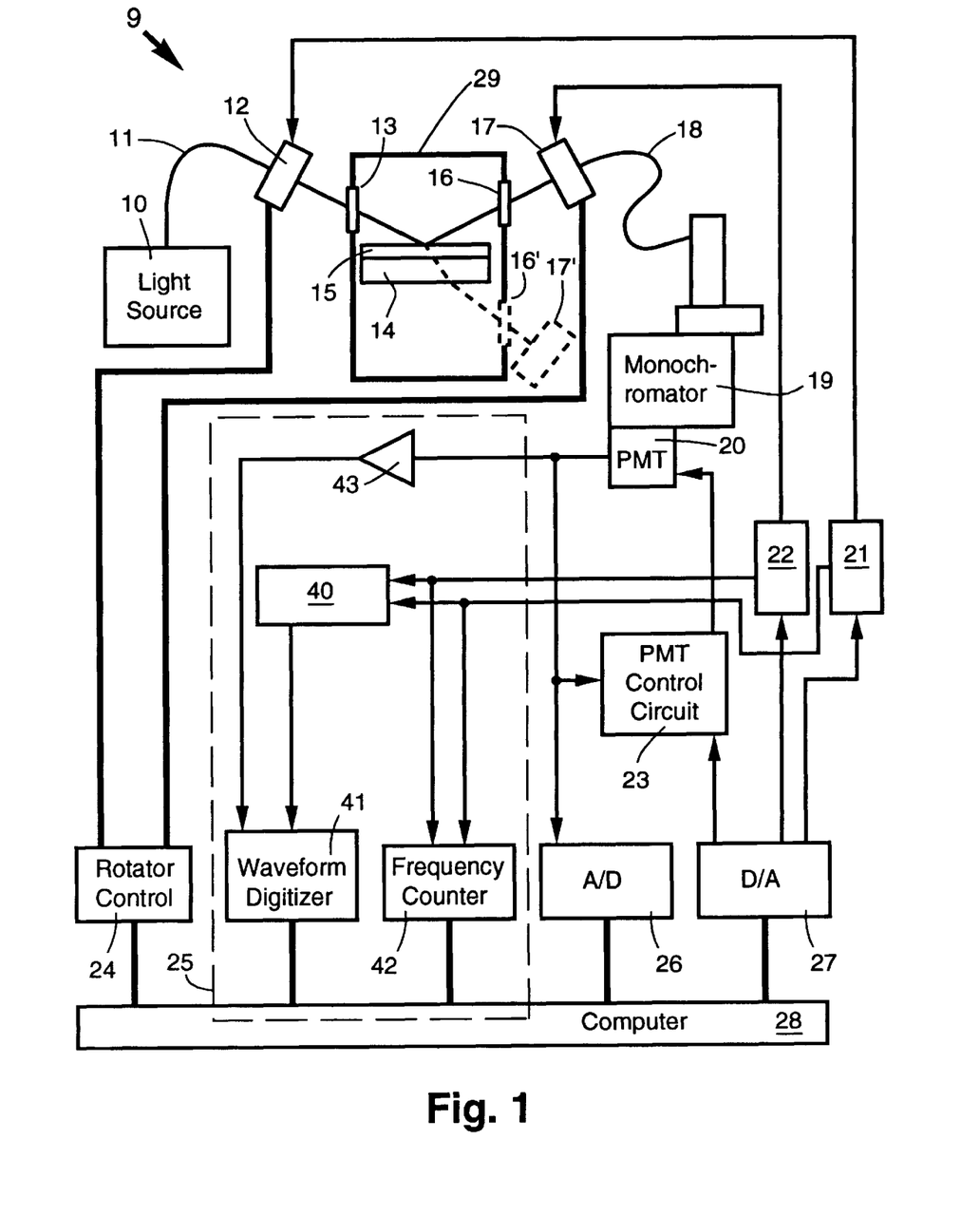
FIG. 1 is a schematic drawing of the two-modulator generalized ellipsometer (2-MGE) and associated control circuitry according to the present invention.
Figure 2:
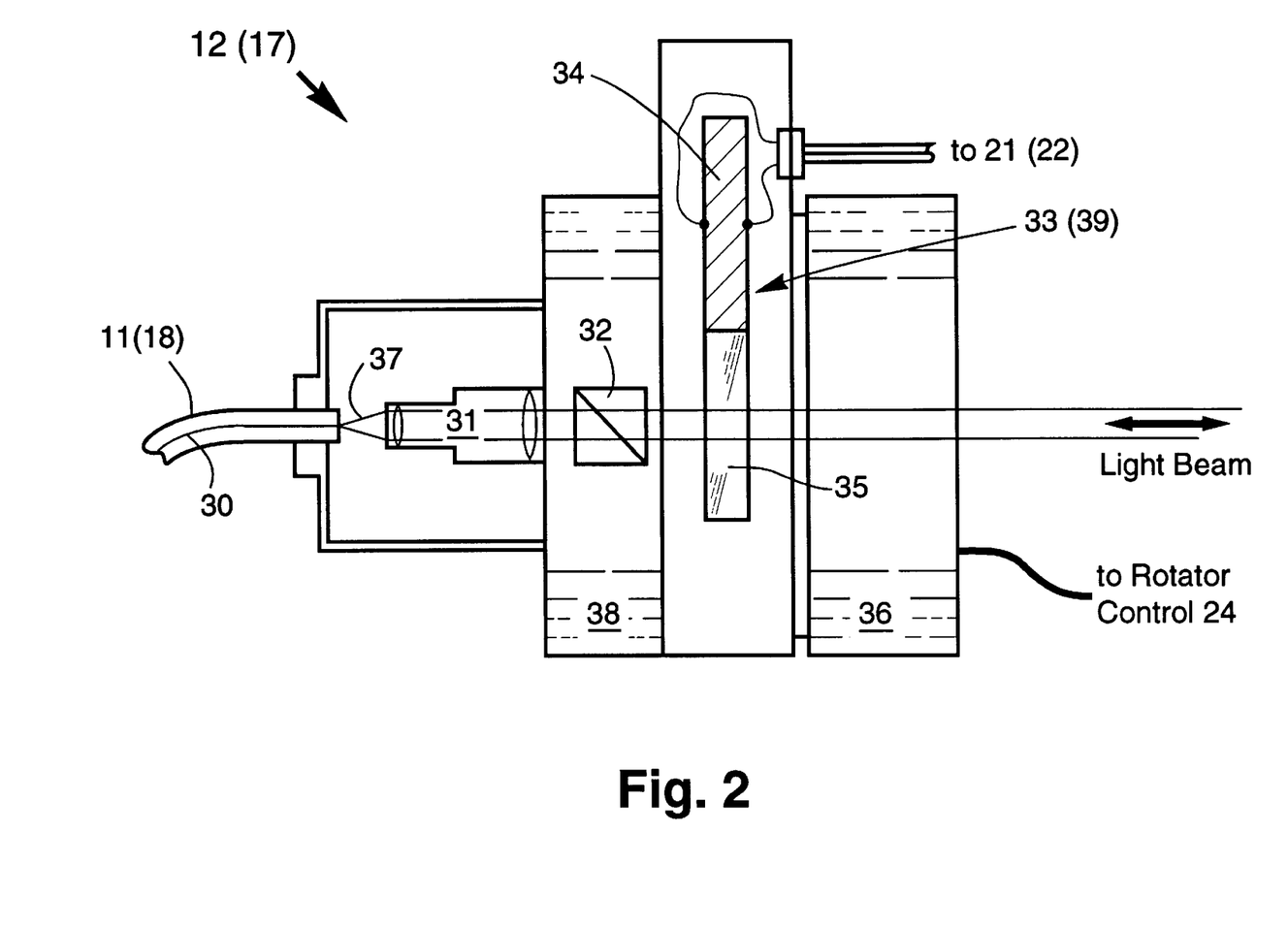

In FIGS. 1 and 2, the two-modulator generalized ellipsometer (2-MGE) comprises a broad spectrum light source 10, such as a 75-watt xenon arc lamp, that is focused onto the large end of a tapered fiber optic 11 using a condensing lens (not shown). The small end of the tapered fiber optic is attached to the light entrance of the polarization state generator (PSG) 12, at the focal point of a 10× microscope objective 31. The condensing lens in the light source housing 10, the fiber optic 11, and the microscope objective 31 comprise a light collimator. In FIG. 2, a cone of light 37 emerges from the end of the fiber optic core 30 at a large angle and enters the microscope objective 31.

In FIG. 2, the collimated light passes left-to-right through a polarizer-photoelastic modulator (PEM) pair comprised of the linear polarizer 32 and photoelastic modulator (PEM) 33, where the PEM 33 is operating at nominally 50 kHz. The photoelastic modulator comprises a crystal quartz bar 34, driven at its resonant frequency by a feedback electronic oscillator (21 in FIG. 1), which causes the fused quartz bar 35, fastened to the crystal quartz bar 34, to vibrate along its long axis. The fused quartz bar 35 is tuned to vibrate along its long axis at the same frequency as the first crystal quartz bar 34. The light beam passes through the central region of the fused quartz bar 35 and thereby undergoes a retardation by virtue of the photoelastic effect that is periodic at the resonant frequency of the first crystal quartz bar 34. The linear polarizer 32 is attached to the PEM 33 using a precision manual rotator 38 and is normally oriented at ±45° with respect to the modulation axis of the PEM 33. The polarizer 32 and 33 are attached to a precision automatic rotator 36. The light beam that passes through this polarizer-PEM pair is dynamically elliptically polarized in that the light polarization will generally be elliptical, but the ellipticity of the light polarization will change at the resonant frequency of the PEM 33.

In FIG. 1, the light beam out of the PSG 12 may or may not pass through a polarization-altering optical element 13, which could be a focusing lens or a window on a vacuum chamber 29 containing the sample 14. After reflection from, or transmission through, the sample 14, as the case may be, the light beam may or may not pass through another polarization-altering optical element 16, which could be another focusing lens or window on the vacuum chamber 29. The sample 14 may or may not have a thin film 15 on its surface. Interaction with the sample alters the polarization of the incident light, changes the ellipticity, and possibly partially depolarizes the light beam. It is assumed that the optical properties of the sample (as defined by the sample Mueller matrix) are time-independent. This means that any time-dependent changes in the sample will be much slower than the resonant frequencies of the PSG PEM 33 and the PSD PEM 39.

The light next passes through the polarization state detector (PSD) 17. PSD 17 is identical to the PSG 12 except for its size and operating frequency, and is also illustrated by FIG. 2. In the PSD 17 of FIG. 2, the light beam passes right-to-left through the PEM 39, which is operating at nominally 60 kHz, and then through a linear polarizer mounted to the PEM 39 at ±45° using a precision manual rotator. The light next passes through a microscope objective, which focuses the light onto the core of the fiber optic 18. The PSD 17 is also attached to an automatic rotator. At this point in its travel, the time-dependent intensity of the light beam is a complicated function of time, and includes the fundamental and harmonics of the PSG PEM 33 and the PSD PEM 39, as well as sum and difference frequencies of the fundamentals and harmonics of the PSG PEM 33 and the PSD PEM 39.

In alternate arrangement, the grating monochrometer 19 may be located between the light source 10 and the PSG 12 to allow the light to be monochromatized before passing through PSG 12. There may be an f# matcher between the output of the optical fiber and the monochromator to change the f# of the fiber optic (nominally f/2) to the f# of the monochromator (nominally f/4). There also may be a filter wheel before the entrance slit of the monochromator to eliminate second order effects of the grating. The light intensity is detected at the output slit using a photomultiplier tube (PMT) 20. Alternatively, a photodiode could be used instead of the PMT for detecting the light intensity.

Even in the ideal case where the PEMs 33, 39 are not strained, this light intensity as measured by the PMT 20 is a very complicated function of time, having the form:

$$I(t)=I_{dc}+I_{X0}X_0+I_{Y0}Y_0+I_{X1}X_1+I_{Y1}Y_1+I_{X0X1}X_0X_1+I_{X0Y1}X_0Y_1+I_{Y0X1}Y_0X_1+I_{Y0Y1}Y_0Y_1, \quad (1)$$

where $I_{dc}$, $I_{X0}$, $I_{Y0}$, $I_{X1}$, $I_{Y1}$, $I_{X0X1}$, $I_{X0Y1}$, $I_{Y0X1}$, and $I_{Y0Y1}$ are time-independent constants and contain the information concerning the Mueller matrix elements of the sample and the embedded trigonometric functions are given by:

$$X_0=\sin(A_0\sin(\omega_0 t+\phi_0)), \quad (2a)$$

$$Y_0=\cos(A_0\sin(\omega_0 t+\phi_0)), \quad (2b)$$

$$X_1=\sin(A_1\sin(\omega_1 t+\phi_1)), \quad (2c)$$

$$Y_1=\cos(A_1\sin(\omega_1 t+\phi_1)), \quad (2d)$$

where $\omega_0$ and $\omega_1$ are the operating frequencies of the photoelastic modulators (nominally 50 and 60 kHz in this case), $A_0$ and $A_1$ are the Bessel angles that are proportional to the amplitude of modulation, and $\phi_0$ and $\phi_1$ are the modulator phases with respect to an external signal. Since the PEMs 33,39 are free running, their operating frequencies and phases may change with room temperature. For the case where $\phi_0=\phi_1=0$, each of these components can be expressed using a Fourier series of sine and cosine terms in which integer Bessel functions are the Fourier coefficients:

$$X_0 = \sin(A_0\sin(\omega_0 t)) = 2\sum_{k=1}^{\infty} J_{2k-1}(A_0)\sin((2k-1)\omega_0 t), \quad (3a)$$

$$Y_0 = \cos(A_0\sin(\omega_0 t)) = J_0(A_0) + 2\sum_{k=1}^{\infty} J_{2k}(A_0)\cos(2k\omega_0 t). \quad (3b)$$

The quantities $A_0$ and $A_1$ are commonly set to 2.4048 radians by adjusting the modulation amplitudes of the PEMs 33, 39. In the Fourier representation of the light intensity, the time-dependent intensity is given by $$I(t) = I_{dc} + \sum_{k=1}^{\infty} R_k[\alpha_k\cos(\Omega_k t) + \beta_k\sin(\Omega_k t)], \quad (4)$$

where $R_k$ are coefficients that depend upon the term selected and include products of the integer Bessel functions $J_n(A_0)$ and/or $J_m(A_1)$. The quantities $\Omega_k$ are harmonics and sum and difference frequencies of the fundamental frequencies of the PEMs. When $A_0=A_1=2.4048$, the coefficients $R_k$ are small for frequencies $\Omega_k$>400 kHz, so the infinite summation quickly converges.

The signal coming from the PMT 20 is a photocurrent, which is converted to a voltage using a preamplifier 43. A feedback control circuit 23 regulates the PMT 20 voltage, so that the PMT 20 dc component of the photocurrent remains constant. This dc current is read using an analog-to-digital converter 26. The time-varying component of the voltage from the preamplifier 43 is digitized using a waveform digitizer 41, where the digitization rate is Δt (typically 1 microsecond) and the number of digitized time points is T (typically 1024). A pulse from a trigger circuit 40 initializes digitization when the phases from the monitor output of the PEM 33, 39 control circuits 21,22 are both 0°±1°. The reference outputs from the modulator control circuits 21,22 are fed into the trigger circuit 40, and into the frequency counter 42. A digital-to-analog converter 27 puts out 0-5 V analog signals which are used to set the modulation amplitudes of the PEMs 33, 39 using the modulator feedback control circuits 21 and 22, and to set the dc current and maximum bias voltage of the PMT 20 using the PMT control circuit 23. The entire instrument is controlled through the computer 28, which interacts with each of the components via the computer bus (not shown). The computer 28 is also used to collect the data and perform the analysis of the I(t) waveform.

In the context of our invention, dc or time-independent quantities are quantities that change much slower than the oscillation periods of the PEMs, which would be on a time scale slower than about 10 milliseconds. Time-dependent quantities are those that change at least as fast as the difference frequency of the PEMs (~10 kHz), which would be on a time scale faster than about 100 microseconds.

The eight coefficients $I_{X0}$, $I_{Y0}$, $I_{X1}$, $I_{Y1}$, $I_{X0X1}$, $I_{X0Y1}$, $I_{Y0X1}$, and $I_{Y0Y1}$ (normalized to the $I_{dc}$ component) are determined from the digitized waveform from waveform digitizer 41 using a Fourier-like analysis. To first order, this normalization is natural, since the PMT bias voltage is continually adjusted to keep $I_{dc}$ constant (with a time constant about 10 milliseconds), but its value is also measured.

Three separate methods of signal analysis may be used with our invention. All require that the phases of the modulators $\phi_0$ and $\phi_1$ be taken into account. Two of these techniques digitize the waveform and utilize the components shown at 25 in FIG. 1, where the acquisition of the waveform is initialized by a trigger pulse from the trigger circuit 40 whenever the PEM monitor signals are in coincidence at $0°\pm1°$. Due to electronic phase shifts, $\phi_0$ and $\phi_1$ will not necessarily be 0.

The first method is complete-period Fourier integration which determines the eight coefficients ($I_{X0}$, $I_{Y0}$, $I_{X1}$, $I_{Y1}$, $I_{X0X1}$, $I_{X0Y1}$, $I_{Y0X1}$, and $I_{Y0X1}$) from the digitized waveform I (of dimension 0:T-1). At least eight frequencies $\Omega_k$ are chosen which are not close to other frequencies in the spectrum waveform (such as $\omega_0$, $\omega_1$, $2\omega_0$, $2\omega_1$, $\omega_0+\omega_1$, $2\omega_0+\omega_1$, $\omega_0+2\omega_1$, $2(\omega_0+\omega_1)$) for the present modulators).

The basis functions for this Fourier integration are 1.0 and the functions sin ($\Omega_k t$) and cos ($\Omega_k t$) for each analyzed frequency $\Omega_k$. If eight frequencies are used, then the basis set contains 17 functions. The analysis of the digitized waveform takes place using the following steps:

1. Construct the basis matrix B of dimension (0:2N, 0:T-1) where $B_{0,i}=1.0$, $B_{2k,i}=\cos(\Omega_k i\Delta t); B_{2k-1,i}=\sin(\Omega_k i\Delta t) k=1,\ldots N; i=0,\ldots T-1$ where N is the number of frequencies incorporated into the analysis, and T $\Delta t$ is the total time captured by the waveform digitizer.

2. Calculate the correction matrix $K=(B B^T)^{-1}$ where K is of dimension (0:2N, 0:2N)

3. Calculate the matrix A=K B I, where A is of dimension (0:2N), and $A_0=I_{dc}; A_{2k}=\alpha_k; A_{2k-1}=\beta_k k=1,\ldots N$ The magnitude of each frequency component is given by $(\alpha_k^2+\beta_k^2)^{1/2}$ (see Eq. 4), but the sign of the component must be determined from the measured phase $\phi_m$ and the relative modulator phases $\phi_0$ and $\phi_1$. The measured phase is $\phi_m$=Arg $(\alpha_k+i\beta_k)$, where the Arg function is the principal value of the argument of $\alpha_k+i\beta_k$, defined between $\pi$ and $-\pi$.

The value of each of the eight coefficients can now be determined from the measured magnitudes, phases, modulator phases $\phi_0$ and $\phi_1$, and integer Bessel functions. For example, if 8 frequencies are used, then $I_{X0}=\text{Sign}(\sin(\phi_m+\phi_0))(\alpha^2+\beta^2)^{1/2}/(2J_1(A_0))\Omega=\omega_0$ (5a)

$I_{Y0}=\text{Sign}(\cos(\phi_m+\phi_0))(\alpha^2+\beta^2)^{1/2}/(2J_2(A_0))\Omega=2\omega_0$ (5b)

$I_{X1}=\text{Sign}(\sin(\phi_m+\phi_1))(\alpha^2+\beta^2)^{1/2}/(2J_1(A_1))\Omega=\omega_1$ (5c)

$I_{Y1}=\text{Sign}(\cos(\phi_m+\phi_1))(\alpha^2+\beta^2)^{1/2}/(2J_2(A_1))\Omega=2\omega_1$ (5d)

$I_{X0X1}=\text{Sign}(\cos(\phi_m+\phi_0+_1))(\alpha^2+\beta^2)^{1/2}/(4J_1(A_0)J_1(A_1))\Omega=\omega+\omega_1$ (5e)

$I_{X0Y1}=\text{Sign}(\sin(\phi_m+\omega_0+2\phi_1))(\alpha^2+\beta^2)^{1/2}/(4J_1(A_0)J_2(A_1))\Omega=\omega+2\omega_1$ (5f)

$I_{Y0X1}=\text{Sign}(\sin(\phi_m+2\omega_0+\omega_1))(\alpha^2+\beta^2)^{1/2}/(4J_2(A_0)J_1(A_1))\Omega=2\omega^0+\omega_1$ (5g)

$I_{Y0Y1}=\text{Sign}(\cos(\phi_m+2\phi_0+2\phi_1))(\alpha^2+\beta^2)^{1/2}/(4J_2(A_0)J_2(A_1))\Omega=2\omega_0+2\omega_1$ (5h)

Since the measured phase and the relative modulator phases are only used to measure the sign of the component of the I vector, they need not be determined very accurately. (T-1) $\Delta t$ is the total time captured by the waveform digitizer.

In our second analysis method, called complete-period embedded trigonometric basis function integration, the waveform is analyzed by using a complete basis set of the embedded trigonometric functions. For this analysis, there are only nine basis functions:

$B_0=1.0$ (6a)

$B_1=\sin(A_0\sin(\omega_0 t+\phi_0))$ (6b)

$B_2=\cos(A_0\sin(\omega_0 t+\phi_0))$ (6c)

$B_3=\sin(A_1\sin(\omega_1 t+\phi_1))$ (6d)

$B_4=\cos(A_1\sin(\omega_1 t+\phi_1))$ (6e)

$B_5=B_1B_3$ (6f)

$B_6=B_1B_4$ (6g)

$B_7=B_2B_3$ (6h)

$B_8=B_2B_4$ (6i)

The analysis is now similar to the first method: Calculate the correction matrix $K=(B B^T)^{-1}$ where K is of dimension (0:8, 0:8), and then the matrix A=K B I, where $A^T=(I_{dc}, I_{X0}, I_{Y0}, I_{X1}, I_{Y1}, I_{X0X1}, I_{X0Y1}, I_{Y0X1}, I_{Y0Y1})$.

The accuracy of both the first and second methods is improved if the number of time points (T) is set to a value that corresponds to nearly an integer number of cycles for each frequency considered in the analysis. Since the phase of the modulators is used only to determine the sign of the coefficients with the first method, they need not be determined accurately. With the second method, accurate determination of the modulator phases is very important.

Figure 3:
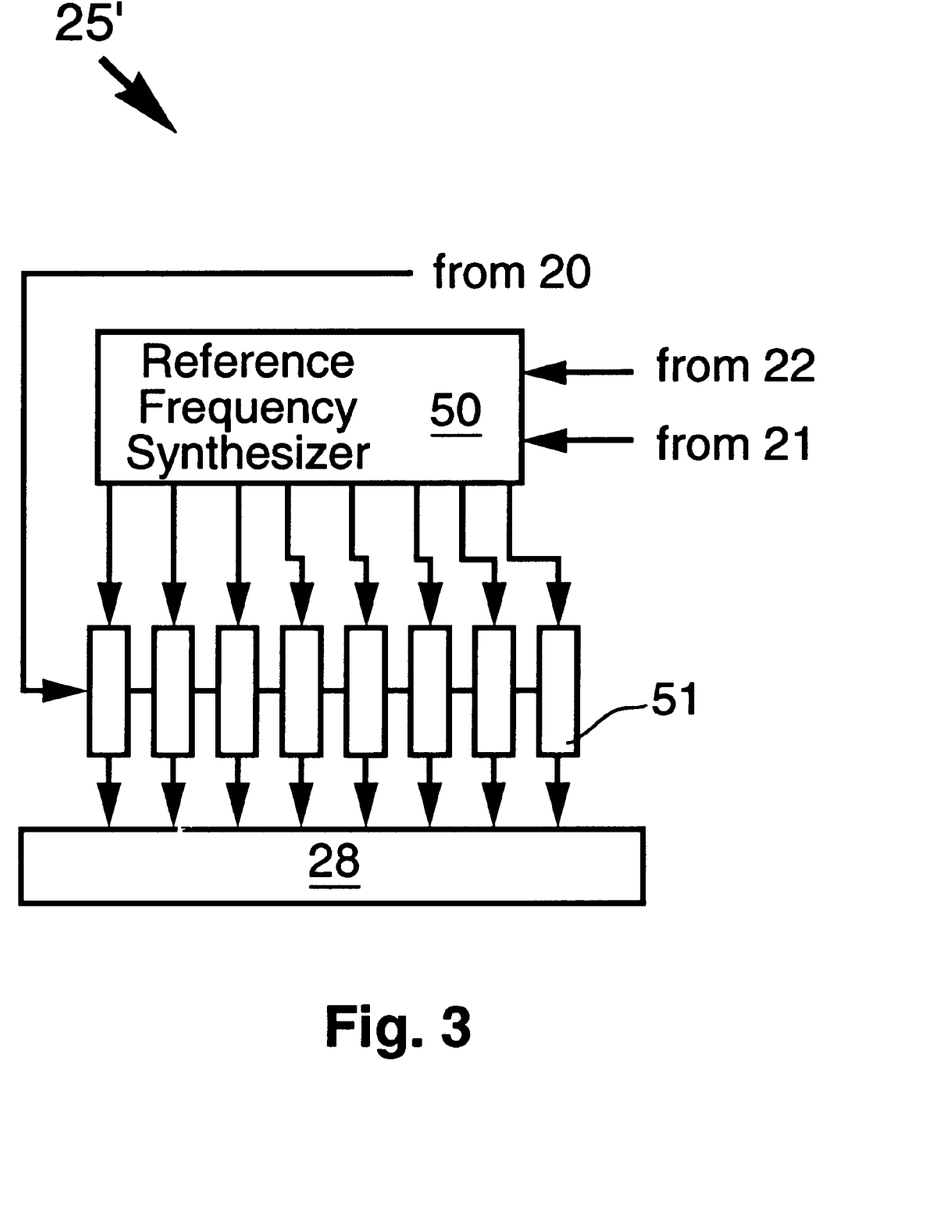
FIG. 3 is a schematic drawing of another analysis circuit for the 2-MGE that uses phase-sensitive detection according to an alternate embodiment of the present invention.

The third preferred mode of signal analysis is the analog version of the first method and is shown at 25' in FIG. 3. It comprises routing the PEM monitor signals from the modulator control circuits 21,22 into a reference frequency synthesizer 50 that generates amplitude-stable reference signals for synchronous detection, either directly from the PEM reference signals, or indirectly by mixing and/or doubling the frequencies of these reference signals to synthesize the harmonics, sum, and difference frequencies mentioned above. The outputs from the reference frequency synthesizer 50 are applied to several phase-sensitive detectors (e.g., lock-in amplifiers) 51, which measure the magnitudes of the selected frequency components $I_{X0}$, $I_{Y0}$, $I_{X1}$, $I_{Y1}$, $I_{X0X1}$, $I_{X0Y1}$, $I_{Y0X1}$, and $I_{Y0Y1}$ of the photocurrent from the PMT 20. As with the previous analysis methods, the modulator phases $\phi_0$ and $\phi_1$ must be included in the determination. One way of doing this is to use a dual lock-in amplifier on each measurement frequency $\Omega$ to record the magnitude $(\alpha^2+\beta^2)^{1/2}$. The phase information is then only be used to determine the sign of the component, as in the first method.

The measured coefficients $I_{X0}$, $I_{Y0}$, $I_{X1}$, $I_{Y1}$, $I_{X0X1}$, $I_{X0Y1}$, $I_{Y0X1}$, and $I_{Y0Y1}$ contain contributions from the modulator static strain. If the static strain is small, then $\sin(A_0\sin(\omega_0 t)+\delta_0)=\sin(A_0\sin(\omega_0 t))+\delta_0\cos(A_0\sin(\omega t))$, (7a)

$\cos(A_0\sin(\omega_0 t)+\delta_0)=\cos(A_0\sin(\omega_0 t))-\delta_0\sin(A_0\sin(\omega_0 t))$, (7b)

and first order corrections can be applied to remove the static strain contributions to the coefficients $I_{X0}$, $I_{Y0}$, $I_{X1}$, $I_{Y1}$, $I_{X0X1}$, $I_{X0Y1}$, $I_{Y0X1}$, and $I_{Y0Y1}$.

If the azimuthal angles of the PEM-polarizer pairs are oriented at $(PEM_0,PEM_1)=(0°,\pm 45°)$, $(\pm 45°,0°)$, $(90°,\pm 45°)$, or $(\pm 45°,90°)$ then the 8 normalized coefficients $I_{X0}$, $I_{Y0}$, $I_{X1}$, $I_{Y1}$, $I_{X0X1}$, $I_{X0Y1}$, $I_{Y0X1}$, and $I_{Y0Y1}$ are sufficient to completely describe systems for which the Mueller-Jones transformation is valid. For more complicated systems requiring all sixteen Mueller matrix elements, four zone measurements, such as $(0°, 45°)$, $(45°,0°)$, $(0°, 0°)$, $(45°, 45°)$ are required.

Calibration of the Instrument

In order for this instrument to measure the 8 normalized coefficients $I_{X0}$, $I_{Y0}$, $I_{X1}$, $I_{Y1}$, $I_{X0X1}$, $I_{X0Y1}$, $I_{Y0X1}$, and $I_{Y0Y1}$ accurately, a calibration of the instrument must be performed. This calibration is done in two parts: First, the 2-MGE is aligned in the straight-through configuration to measure the characteristics of the PSG 12 and the PSD 17. This includes the angular orientation of the polarizer with respect to the longitudinal axis of the PEMs ($\theta_{b0}$ and $\theta_{b1}$), the magnitude of the wavelength-dependent control voltage $V_{m0}(\lambda)$ and $V_{m1}(\lambda)$ needed to generate the PEM amplitudes such that $A_0=A_1=2.4048$, and the static strain-induced retardation $\delta_0(\lambda)$ and $\delta_1(\lambda)$ of each of the PEMs, where $A_0$, $A_1$, $\delta_0$, and $\delta_1$ are shown explicitly as functions of wavelength $\lambda$. The second calibration measures the azimuthal angles of the PSG 12 and the PSD 17 with respect to the plane of incidence $\theta_{m0}$ and $\delta_{m1}$ defined by the sample surface.

For the first calibration, the ellipsometer is aligned in the straight-through configuration, where the coefficients of Eq. 1 are given by:

$$I_{X0}=0, \tag{8a}$$

$$I_{Y0}=P_{01}[J_0(A_1)\cos(2\theta_m)-2\sin(2\theta_m)\epsilon_{b1}], \tag{8b}$$

$$I_{X1}=0, \tag{8c}$$

$$I_{Y1}=P_{01}[J_0(A_0)\cos(2\theta_m)+2\sin(2\theta_m)\epsilon_{b0}], \tag{8d}$$

$$I_{X0X1}=-P_{01}, \tag{8e}$$

$$I_{X0Y1}=-P_{01}[\delta_1+\delta_0\cos(2\theta_m)], \tag{8f}$$

$$I_{Y0X1}=-P_{01}[\delta_0+\delta_1\cos(2\theta_m)], \tag{8g}$$

$$I_{Y0Y1}=P_{01}\cos(2\theta_m), \tag{8h}$$

where $P_{01}=\sin(2\theta_{b0})\sin(2\theta_{b1})=\pm 1$. The angle $\downarrow_m$ is the angle of the PSG with respect to the PSD, and $\epsilon_{b0}$ and $\epsilon_{b1}$ are the errors of $\theta_{b0}$ and $\theta_{b1}$ from $\pm 45°$. The quantities $J_0(A_0)$ and $J_0(A_1)$ are the $0_{th}$ order integer Bessel functions at angles $A_0$ and $A_1$, where it is assumed that $A_0$ and $A_1$ are near 2.4048 radians, where $J_0(A_0)$ and $J_0(A_1)$ are small. These equations identify the three calibration parameters that can be measured for each PEM: $\delta_i$, $A_i$, and $\epsilon_{bi}$, where i=0 or 1.

For the Bessel angle A near 2.4048, a first-order Taylor series can be used to approximate $J_0(A)$:

$$J_0(A)=-0.5196(2.4048-A), \tag{9}$$

so measuring $J_0(A)$ when A~2.4 is equivalent to measuring A. The objective of this calibration is to determine the control voltage from the digital-to-analog converter required to set A=2.4048. Because the retardation of the PEMs exhibits dispersion with wavelength or photon energy E, the modulator control voltage $V_m$ required to give a Bessel angle A is of the form:

$$V_{mi}(E) = \frac{K_v A_i}{E \sum_{k=0}^{\infty} \gamma_{ki} E^{2k}}, \tag{10}$$

where E is the photon energy, $K_v$ is a constant. The sum converges rapidly, so only two to four terms are normally required. The static strain is a similar function of photon energy because of dispersion, and is given by:

$$\delta_i(E) = K_{\delta i} E \sum_{k=0}^{\infty} \gamma_{ki} E^{2k}. \tag{11}$$

The second calibration required for accurate measurements with the 2-MGE is to measure the azimuthal angles of the PSG 12 and the PSD 17 with respect to the plane of incidence. This measurement is performed with the sample in place, and it is assumed that the sample is isotropic. The 2-MGE is configured such that both the PSG and the PSD are aligned nearly parallel to the plane of incidence ($\theta_{m0}\cong\theta_{m1}\cong 0$). In this configuration, the $I_{Y0}$ and $I_{Y1}$ are given to first order in the error parameters by:

$$I_{Y0}=-\sin(2\theta_{b0})[N\sin(2\theta_{m0})-\sin(2\theta_{b1})C\,J_0(A_1)], \tag{12a}$$

$$I_{Y1}=-\sin(2\theta_{b1})[N\sin(2\theta_{m1})-\sin(2\theta_{b0})C\,J_0(A_0)], \tag{12b}$$

where $N=\cos(2\psi)$ and $C=\sin(2\psi)\cos(\Delta)$, $\psi$ and $\Delta$ are the conventional ellipsometric angles. If a wavelength is selected where N is large and if $J_0(A_0)=J_0(A_1)=0$, then $I_{Y0}$ and $I_{Y1}$ are directly proportional to the errors in $\theta_{m0}$ and $\theta_{m1}$, respectively. Alternatively, if the $J_0(A_0)=J_0(A_1)=0$ assumption cannot be made, then a calibration can be made in which $I_{Y0}$ and $I_{Y1}$ are alternately nulled out by setting either $\theta_{b1}$ or $\theta_{b0}$ to 0 to obtain an intensity coefficient proportional to the error in $\theta_{m0}$ and $\theta_{m1}$. The zero references for $\theta_{m0}$ and $\theta_{m1}$ are readily established by either method.

While there has been shown and described what is at present considered the preferred embodiments of the invention, it will be obvious to those skilled in the art that various changes and modifications may be made therein without departing from the scope of the invention as defined by the appended claims.

We claim:

1. A two-modulator generalized ellipsometer for measuring up to all sixteen time-independent Mueller matrix elements of a sample comprising:

a) means for producing a light beam;

b) a polarization state generator (PSG) comprising a polarizer and a free-running photoelastic modulator (PEM), said PSG PEM operating at a first resonant frequency for dynamically elliptically polarizing said light beam before interaction with the sample;

c) a polarization state detector (PSD) comprising a free-running photoelastic modulator(PEM) and a polarizer, said PSD PEM operating at a second resonant frequency for polarizing said light beam after interaction with the sample, the resonant frequency of said PSD PEM differing from that of said PSG PEM;

d) a light detector for detecting the time-dependent intensity of said light beam from said PSD and converting said intensity to a time-dependent electrical waveform;

e) means for measuring the frequency of each PEM;

f). means for measuring the phase of each PEM;

g). means for digitizing said time-dependent electrical waveform; and h). means for determining up to nine of the sixteen time-independent Mueller matrix elements of the sample from said digitized time-dependent electrical waveform, said measured frequency of each PEM, and said measured phase of each PEM.

2. The ellipsometer of claim 1 wherein said means for producing a light beam is a single wavelength laser.

3. The ellipsometer of claim 1 wherein said means for producing a light beam is a multiple wavelength laser.

4. The ellipsometer of claim 1 wherein said means for producing a light beam is a spectral light source and collimator.

5. The ellipsometer of claim 4 wherein said spectral light source is an arc lamp.

6. The ellipsometer of claim 4 wherein said collimator comprises a condensing lens, fiber optic and a microscope objective.

7. The ellipsometer of claim 4 further including a means for monochromatizing said light beam.

8. The ellipsometer of claim 7 wherein said means for monochromatizing said light beam is a grating monochromator.

9. The ellipsometer of claim 7 wherein said means for monochromatizing said light beam is placed in the light path such that the light is monochromatized before the PSG.

10. The ellipsometer of claim 7 wherein said means for monochromatizing said light beam is placed in the light path such that the light is monochromatized after said PSD but before said light detector.

11. The ellipsometer of claim 1 wherein said light detector is a photomultiplier tube (PMT).

12. The ellipsometer of claim 11 wherein the photocurrent from said PMT is fed into a control circuit which regulates the output current of said PMT.

13. The ellipsometer of claim 1 wherein said light detector is a photodiode.

14. The ellipsometer of claim 1 further including a chamber for containing the sample, said chamber having windows for the ingress and egress of said light beam.

15. The ellipsometer of claim 1 further including a lens for focussing the light onto the sample and possibly recollimating the reflected or transmitted light after the sample.

16. A method for determining up to nine of the sixteen time-independent Mueller matrix elements of a sample comprising the steps of:

a) providing a light beam;

b) dynamically elliptically polarizing said light beam using a polarizer and a free-running photoelastic modulator (PEM) as a polarization state generator (PSG);

c) impinging said dynamically elliptically polarized light beam onto the sample for interaction therewith to change the polarization of said light beam exiting the sample;

d) dynamically changing the polarization of said light beam exiting the sample using a free-running photoelastic modulator (PEM) and a polarizer as a polarization state detector (PSD) resulting in a time-dependent light beam exiting from said PSD;

e) selecting a small band of wavelengths from said time-dependent light beam from said PSD to produce a time-dependent quasi-monochromatic light beam;

f) converting said time-dependent quasi-monochromatic light beam intensity to a time-dependent electrical waveform by means of a light detector; and g) analyzing said time-dependent electrical waveform to determine up to nine time-independent intensity coefficients, which are linear combinations of the sixteen time-independent Mueller matrix elements of the sample.

17. The method of claim 16 wherein the step of analyzing said time-dependent electrical waveform comprises maintaining one of said nine time-independent intensity coefficients invariant and normalizing the remaining eight of said nine time-independent intensity coefficients with respect to said invariant time-independent intensity coefficient.

18. The method of claim 17, wherein the said up to eight of said nine time-independent intensity coefficients are determined by the steps of:

a) triggering a waveform digitizer by means of a circuit which puts out a pulse when the phase of said PSG PEM and the phase of said PSD PEM are at known values;

b) digitizing said time-dependent electrical waveform with said waveform digitizer;

c) transferring said digital waveform to a digital computer; and d) analyzing said digitized waveform by complete-period Fourier integration.

19. The method of claim 17, wherein the said up to eight of said nine time-independent intensity coefficients are determined by the steps of:

a) triggering a waveform digitizer by means of a circuit which puts out a pulse when the phase of said PSG PEM and the phase of said PSD PEM are at known values;

b) digitizing said time-dependent electrical waveform with said waveform digitizer;

c) transferring said digital waveform to a digital computer; and d) analyzing said digitized waveform by complete-period embedded trigonometric basis function integration.

20. The method of claim 17, wherein the said up to eight of said nine time-independent intensity coefficients are determined by the steps of:

a) generating reference waveforms of the harmonics of each of said PEMs as well as the sum and difference frequencies; and b) using phase-sensitive detectors to determine the time-independent Fourier coefficients of said time-dependent electrical waveform by synchronous demodulation using said reference waveforms.

21. The method of claim 16 comprising the additional steps of changing the azimuthal angles of the PSG and/or the PSD and measuring up to the other seven of said sixteen time-independent Mueller matrix elements of the sample.

22. A two-modulator generalized ellipsometer for measuring up to all sixteen time-independent Mueller matrix elements of a sample comprising:

a) means for producing a light beam;

b) a polarization state generator (PSG) comprising a polarizer and a free-running photoelastic modulator (PEM), said PSG PEM operating at a first resonant frequency for dynamically elliptically polarizing said light beam before interaction with the sample;

c) a polarization state detector (PSD) comprising a free-running photoelastic modulator(PEM) and a polarizer, said PSD PEM operating at a second resonant frequency for polarizing said light beam after interaction with the sample, the resonant frequency of said PSD PEM differing from that of said PSG PEM;

d) a light detector for detecting the time-dependent intensity of said light beam from said PSD and converting said intensity to a time-dependent electrical waveform;

e) means for generating a plurality of amplitude-stable reference frequencies from the resonant frequencies of said PSG PEM and said PSD PEM;

f) means for extracting selected frequency components of said time-dependent electrical waveform based upon said reference frequencies; and g) means for determining up to nine of the sixteen time-independent Mueller matrix elements of the sample from said extracted selected frequency components.

* * * * *